(12) United States Patent
Madhusudhan

(10) Patent No.: US 7,074,568 B2
(45) Date of Patent: Jul. 11, 2006

(54) MOLECULAR DIAGNOSIS OF ATYPICAL MYCOBACTERIAL INFECTIONS

(75) Inventor: Kunapuli T. Madhusudhan, Ames, IA (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 319 days.

(21) Appl. No.: 10/692,905

(22) Filed: Oct. 25, 2003

(65) Prior Publication Data

US 2005/0214770 A1    Sep. 29, 2005

Related U.S. Application Data

(60) Provisional application No. 60/421,451, filed on Oct. 26, 2002.

(51) Int. Cl.
   *C12Q 1/68*      (2006.01)
   *C12P 19/34*     (2006.01)
   *C07H 21/04*     (2006.01)
(52) U.S. Cl. .................. 435/6; 536/24.32; 435/91.2
(58) Field of Classification Search .............. 435/6, 435/91.2; 536/24.32, 24.33
   See application file for complete search history.

(56) References Cited

U.S. PATENT DOCUMENTS

| | | | | |
|---|---|---|---|---|
| 5,731,150 A | * | 3/1998 | Sandhu et al. ................. | 435/6 |
| 5,776,693 A | * | 7/1998 | Guesdon et al. ............... | 435/6 |
| 6,670,130 B1 | * | 12/2003 | Kim et al. ..................... | 435/6 |

* cited by examiner

*Primary Examiner*—Kenneth R. Horlick
*Assistant Examiner*—Angela Bertagna
(74) *Attorney, Agent, or Firm*—Angela Foster, Esq.

(57) ABSTRACT

The present invention provides methods for diagnosing mycobacteria other than tuberculosis (MOTT) infections in patients comprising amplifying the internal transcribed spacer sequence (ITSS) of 16S-23S rDNA of MOTT with primers that amplify MOTT but not *Mycobacteria Tuberculosis* (MTB). The present invention also provides a method for differentiating between MOTT and MTB infections comprising amplifying MOTT with primers that amplify MOTT but not MTB; amplifying MTB with primers that amplify MTB but not MOTT; and detecting approximately 130 base pair product indicative of MOTT and approximately 180 base pair product indicative of MTB.

45 Claims, 4 Drawing Sheets

SEQUENCE LISTING

```
<160> NUMBER OF SEQ ID NOS: 6

<210> SEQ ID NO 1
<211> LENGTH: 18
<212> TYPE: DNA
<213> ORGANISM: Artificial
<220> FEATURE:
<223> OTHER INFORMATION: Synthetic sequence from any source

<400> SEQUENCE: 1
ggctgtgggt agcagacc                                                 18

<210> SEQ ID NO 2
<211> LENGTH: 18
<212> TYPE: DNA
<213> ORGANISM: Artificial
<220> FEATURE:
<223> OTHER INFORMATION: Synthetic sequence from any source

<400> SEQUENCE: 2
cgggtccaga tggcttgc                                                 18

<210> SEQ ID NO 3
<211> LENGTH: 18
<212> TYPE: DNA
<213> ORGANISM: Artificial
<220> FEATURE:
<223> OTHER INFORMATION: Synthetic sequence from any source
<220> FEATURE:
<221> NAME/KEY: R
<222> LOCATION: (15)..(18)
<223> OTHER INFORMATION: R denotes  A or G

<400> SEQUENCE: 3
aaggagcacc accaraar                                                 18
```

-continued

```
<210> SEQ ID NO 4
<211> LENGTH: 20
<212> TYPE: DNA
<213> ORGANISM: Artificial
<220> FEATURE:
<223> OTHER INFORMATION: Synthetic sequence from any source
<220> FEATURE:
<221> NAME/KEY: R and Y
<222> LOCATION: (7)..(14)
<223> OTHER INFORMATION: Y denotes C or TR denotes A or G

<400> SEQUENCE: 4
gtgttgyctc aggrcccaat                                              20

<210> SEQ ID NO 5
<211> LENGTH: 20
<212> TYPE: DNA
<213> ORGANISM: Artificial
<220> FEATURE:
<223> OTHER INFORMATION: Synthetic sequence from any source

<400> SEQUENCE: 5
ccatttccca gccgaatgag                                              20

<210> SEQ ID NO 6
<211> LENGTH: 20
<212> TYPE: DNA
<213> ORGANISM: Artificial
<220> FEATURE:
<223> OTHER INFORMATION: Synthetic sequence from any source

<400> SEQUENCE: 6
accaccaagc agggtgacaa                                              20
```

MOLECULAR DIAGNOSIS OF ATYPICAL MYCOBACTERIAL INFECTIONS

1. RELATED APPLICATION

Figure 1:
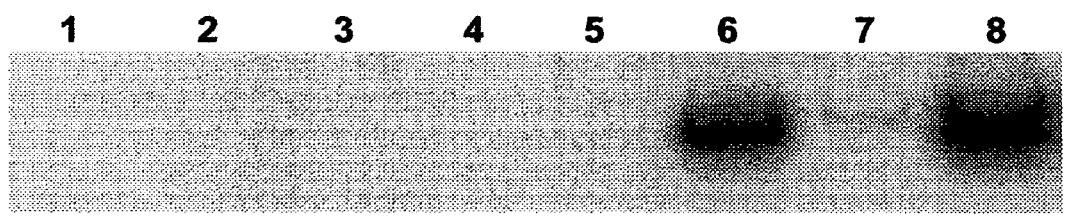

This application claims the benefit of U.S. Provisional Application No. 60/421,451, filed Oct. 26, 2002.

2. FIELD OF INVENTION

The present invention relates to the detection of atypical mycobacteria in biological samples. More specifically, this invention provides methods for rapidly diagnosing atypical mycobacteria infections directly from patient samples using primers generated to the internal transcribed spacer sequence of 16S-23S rDNA that specifically amplify mycobacteria other than tuberculosis (MOTT).

3. BACKGROUND OF THE INVENTION

It is estimated that there are 8 to 10 million new cases of pulmonary tuberculosis causing approximately 3 million deaths per year, worldwide, making tuberculosis one of the foremost causes of death due to infection. *Mycobacterium tuberculosis*, the etiological agent of tuberculosis, is an acid-fast, non-motile, rod shaped bacterium. As a result of recent increases in the number of immunocompromised and immunosuppressed patients, MOTT infections are also increasing. For example, infections by *M. avium* complex (MAC), *M. fortuitum, M. chelonae, M. kansasii* and several other nontuberculosis mycobacteria referred to as atypical mycobacteria or MOTT are opportunistic pathogens in patients infected with HIV as well as in other immune compromised patients. MOTT species are the etiological agents of chronic pulmonary disease, lymphadenitis, skin and soft-tissue infections, and opportunistic infections in man. MOTT are present in the environment and infect animals as well as humans. Unlike the *M. tuberculosis* (MTB) complex (*M. tuberculosis, M. africanum, M. microtii* and *M. bovis*), molecular methods for rapid detection and identification of MOTT species do not exist.

Conventional methods for the diagnosis of mycobacterial infections involve direct acid-fast staining and organism cultivation, followed by biochemical and morphological assays to confirm the presence of mycobacteria and identify the species. Typical diagnostic methods using conventional culture methods are time-consuming and can take as long as six weeks. Automated culturing systems such as the BACTEC™ system (Becton Dickinson Diagnostic Instrument Systems, Sparks, Md.) can decrease the detection time of mycobacteria to one or two weeks. However, once detected, culturing these slow-growing microorganisms in the presence of antibiotics to determine their drug susceptibility requires several additional weeks. Therefore, a need to further reduce the time required to diagnose mycobacterial infections to provide prompt treatment of mycobacterial infections exists.

Because of important clinical significances of MOTT, it is desirable to develop a method that can quickly and efficiently diagnose and differentiate MTB and MOTT. Unfortunately, the ability to quickly diagnose MOTT in the early stages of infection based on clinical testing is lacking. Presently, a combination of clinical findings and identification of acid-fast bacteria by microscopy in patient samples are by far the most rapid and cost-effective detection methods. However, these tests yield poor sensitivity and specificity and definitive diagnosis by culture is still particularly difficult to determine quickly because it takes about 2 to 8 weeks to grow the culture and gather all data (Springer et al., 1996 *J. Clin. Microbiol.* 34:296–303 and Wayne et al., 1991). Moreover, some mycobacterial isolates cannot be accurately identified using standard biochemical test alone. Gas chromatography and high performance liquid chromatography (HPLC) provide an accurate identification but often require culture isolates or larger numbers of bacilli (Ramos, 1994 *J. Chromatgr.* 32:219–227). A commercially available non-isotopic Accuprobe method (GEN-PROBE, Inc.) provides species-specific oligonulceotides probes that hybridize against the RNA of *M. avium, M. intracellulare, M. gordonae* and *M. kansaii*. However, this test is only applicable on cultures and cannot be used directly on patient samples (Lebrun et al., 1994 *J. Clin. Microbiol.* 30:2476–2478).

Molecular methods that provide quick and rapid diagnosis of MOTT in clinical specimens are not available. Available PCR-based methods for diagnosing mycobacterial infections often require considerable time or dedicated equipment for a single test (Yule, 1994 *Biotechnol.* 12:1335–7 and Eisenach et al., 1991 *Am. Rev. Respir. Dis.* 144:1160–3). Methods for identifying rapidly growing mycobacteria using restriction fragment length polymorphism (RFLP) of MOTT DNA and other techniques involving complex methodology are not suitable for clinical testing environments (Telenti et al., 1993 *J. Clin. Microbiol.* 31:175–8; Roth et al, 2000 *J. Clin. Microbiol* 38:1094–1104; Ringuet et al., 1999 *J. Clin. Microbiol* 37:852–857 and Avaniss-Aghajani et al., 1996 *J. Clin. Microbiol* 34:98–102). Further, methods such as multiplex PCR-based assays followed by reverse cross-blot hybridization (Kox et at., 1997 *J. Clin. Microbiol.* 35:1492–1498) or methods that differentiate mycobacteria species by amplifying the superoxide dismutase gene (Zolg et al., 1997 *J. Clin. Microbiol.* 32:2801–2812) used for identifying mycobacteria have several clinical disadvantages. In particular, methods requiring hybridization of nucleic acids extracted from patient samples against species-specific probes can only recognize a specific species of MOTT and require large sample volumes or quantities. Moreover, species-specific methods designed for detecting MTB and *M. avium* in clinical samples (Stauffer et al., 1998 *J. Clin. Microbiol.* 36:614–617 and Emler et al., 2001 *J. Clin. Microbiol.* 39:2687–2689) or PCR amplification techniques for differentiating *M. avium* and *M. intracellulare* (Chen et al., 1996 *J. Clin. Microbiol.* 34:1267–1269 and Kulski et al, 1995 *J. Clin. Microbiol.* 33:668–674), have limited diagnostic utility because these methods differentiate only two species. Therefore, a molecular method capable of diagnosing several MOTT species in both fresh and archival tissue samples in a single test is needed. The present invention not only provides a more rapid method for detecting and differentiating MOTT and MTB, it also significantly decreases the waiting time for growing culture isolates and eliminates the requirement for larger numbers of bacilli.

Discussion or citation of a reference herein shall not be construed as an admission that such reference is prior art to the present invention.

4. SUMMARY OF THE INVENTION

This invention uses sequences of the internal transcribed spacer sequence (ITSS) of 16S-23S rDNA of mycobacteria to identify MOTT and distinguish them from MTB. It was not known until the present invention whether amplification of specific sequences to ITSS of mycobacteria would result in fragments of MOTT and, if so, whether or not these fragments could be used to distinguish MTB from MOTT. It was also unknown whether or not this ITSS generated fragment could be used to distinguish specific species of MOTT. Moreover, classical methods for identification of mycobacteria rely on acid-fast staining of bacilli followed by cultures and biochemical testing which could take as long as 8 weeks to speciate an isolate. Accordingly, the present invention provides a method for diagnosing and identifying infections caused by MOTT or MTB species in a patient sample in a single test in less than 24 hours.

Depending on clinical presentation of a case, physicians often request a clinical laboratory to identify or determine the presence of MOTT in patient samples that are negative for MTB. Therefore, one aspect of the present invention provides a method for detecting MOTT species in a patient sample comprising amplifying MOTT nucleic acid with primers generated to the ITSS of MOTT species and detecting approximately a 130 base pair (bp) amplified product indicating the presence of MOTT in a patient sample.

This invention also provides methods for detecting and differentiating infections caused by MOTT species comprising amplifying MOTT nucleic acid with primers generated to the ITSS of MOTT species and/or *Mycobacterium chelonae;* separating the amplified nucleic acid products; and detecting approximately a 130 base pair (bp) amplified product indicating the presence of MOTT and/or approximately 190 bp indicating the presence of *Mycobacteria chelonae* in a patient sample.

The present invention further provides a method for detecting and differentiating infections caused by MOTT and MTB comprising amplifying nucleic acid with primers generated to the ITSS of MOTT species and primers generated to *Mycobacteria tuberculosis;* separating the amplified nucleic acid products; and detecting approximately a 130 base pair (bp) amplified product indicating the presence of MOTT and/or approximately 180 bp indicating the presence of *M. tuberculosis* in a patient sample.

It is a further object of the present invention to provide diagnostic kits for determining whether a patient is infected with MOTT, MTB or *M. chelonae* comprising 3 primer sets labeled with different detectable labels which are used to amplify MTB or MOTT or *M. chelonae* from a nucleic acid molecule of a sample and a reagent for detecting the labels.

5. DETAILED DESCRIPTION OF THE FIGURES

FIG. 1 shows an autoradiogram of an 8% native polyacrylamide gel revealing the amplification product of the ITSS of mycobacteria with MOTT primers in 100 µl reactions. Lane (1) negative control containing all reaction components and no template DNA; Lane (2) purified *M. bovis* genomic DNA (10 ng); Lane (3) purified *M. tuberculosis* H37Rv genomic DNA (10 ng); Lane (4) purified *M. fortuitum* genomic DNA (10 ng); Lane (5) purified *M. chelonae* genomic DNA (10 ng); Lane (6) purified *M. avium* genomic DNA (10 ng); Lane (7) purified *M. kansaii* genomic DNA (0.01 ng); and Lane (8) purified *M. scrofulaceum* genomic DNA (0.1 ng ).

Figure 2:
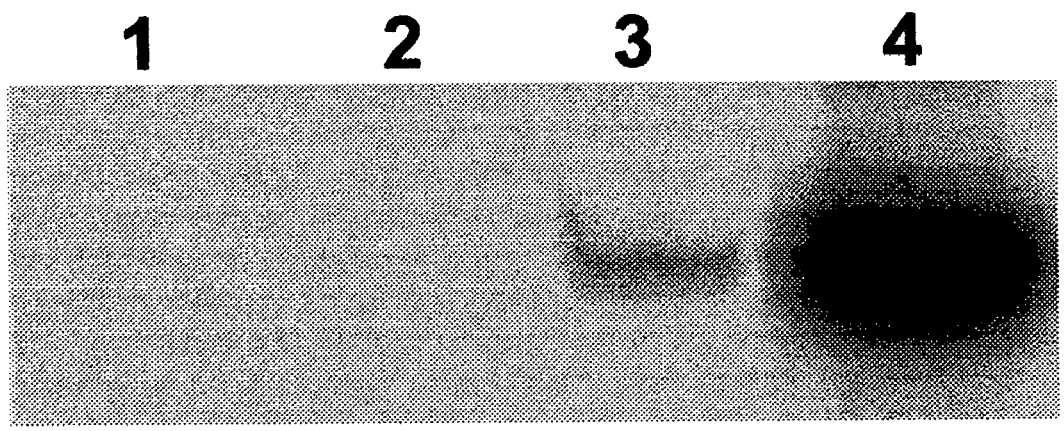

FIG. 2 shows an autoradiogram of an 8% native polyacrylamide gel revealing the amplification of genomic DNA extracted from patient samples using MOTT primers. Lane (1) negative control containing all reaction components and no template DNA; Lane (2) negative acid-fast sputum smear; Lane (3) acid-fast positive pleural fluid; and Lane (4) positive control (*M. avium* genomic DNA).

Figure 3:
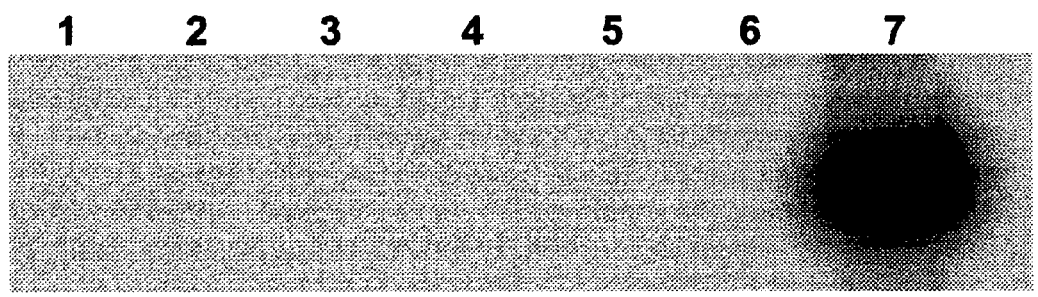

FIG. 3 shows an autoradiogram of an 8% native polyacrylamide gel revealing the amplification product of the ITSS of mycobacteria with *M. chelonae* (MC) primers in 100 µl reactions. Lane (1) negative control containing all reaction components and no template DNA; Lane (2) purified *M avium* genomic DNA (10 ng); Lane (3) purified *M. scrofulaceum* genomic DNA (10 ng); Lane (4) purified *M. bovis* genomic DNA (10 ng); Lane (5) purified *M. tuberculosis* H37Rv genomic DNA (10 ng); Lane (6) purified *M. fortuitum* genomic DNA (10 ng); and Lane (7) purified *M. chelonae* genomic DNA (0.01 ng).

Figure 4:
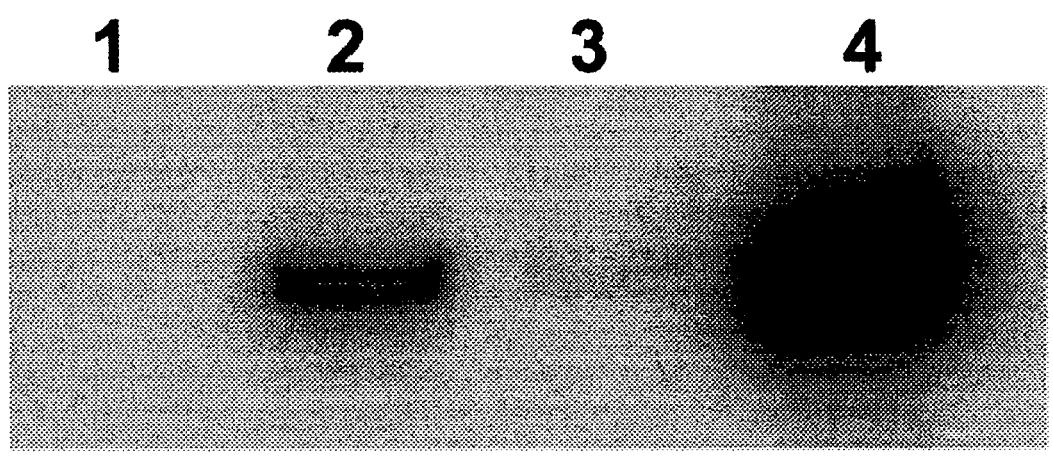

FIG. 4 shows an autoradiogram of an 8% native polyacrylamide gel revealing the amplification of genomic DNA extracted from patient samples using *M. chelonae* (MC) primers. Lane (1) negative control containing all reaction components and no template DNA; Lane (2) BacTec bottle fluid (acid-fast smear positive); Lane (3) archival tissue sections; and Lane (4) positive control (*M. chelonae* genomic DNA).

6. DETAILED DESCRIPTION OF THE INVENTION

This section presents a detailed description of the invention and its applications. This description is by way of several exemplary illustrations, in increasing detail and specificity, of the general methods of this invention. These examples are non-limiting, and related variants will be apparent to one of skill in the art.

Although, for simplicity, this disclosure often makes references to humans it will be understood by those skilled in the art that the methods of the invention are also useful for the analysis of any animal species. Since mycobacteria infect both human and non-human animal species, one skilled in the art will recognize that the methods of the present invention are equally applicable to both human and animals such as livestock or agriculturally important animals.

The description of the invention, for simplicity, is largely in terms of enzymatic amplification. However, the methods of the invention are also applicable, as will be apparent to one skilled in the art, by any method of amplification well known to those of skill in the art. Such methods of amplification include, for example enzymatic amplification and amplification using conventional cloning techniques well known to those skill in the art. In one embodiment of this invention, the amplification is facilitated by enzymatic amplification, e.g., by means of the polymerase chain reaction using primer pair sets. The method of polymerase chain reaction is well known to those of skill in the art.

It should be understood that various changes and modifications to the presently preferred embodiments described herein will be apparent to those skilled in the art. Such changes and modifications can be made without departing from the spirit and scope of the present invention and without diminishing its attendant advantages.

Prior to the present invention, methods used for identifying MOTT species included a chemiluminescent labeled AccuProbe (DNA oligonucleotide) method developed by GEN PROBE, Inc., requiring nucleic acid probes to specifically align and associate to form stable double-stranded complexes with rRNA of a targeted mycobacteria organism followed by detection of the resulting hybrid nucleic acid using a luminometer. Moreover, the AccuProbe method uses culture isolates and cannot be used on patient samples.

Therefore, one embodiment of the present invention provides a method for detecting MOTT comprising obtaining a sample that contains nucleic acid; amplifying the nucleic acid in the sample with primers having the nucleic acid sequence SEQ. ID. NO.: 3 and SEQ. ID. NO.: 4; and detecting amplified nucleic acid products produced in the amplification step, thereby detecting MOTT in the sample.

The samples may comprise clinical samples, isolated nucleic acids or isolated microorganisms. Clinical samples are in the form of a biological fluid or tissue (e.g., sputum, bronchial washings, gastric washings, spinal or synovial or peritoneal or pericardial fluids, blood, milk, lymph, skin, bone marrow, and soft tissues). In a preferred embodiment, the sample is selected from the group consisting of fresh/archival tissues, gastric washings, spinal or synovial or peritoneal or pericardial fluids, blood, milk, lymph, skin, bone marrow, bronchial washes, bronchial washings, sputum and blood.

Nucleic acid is DNA, RNA or mRNA, single-stranded or double-stranded.

The term "probe" or "primer" has the same meaning herein, namely, an oligonucleotide fragment. The term "oligonucleotide" as used in herein refers to a molecule compound of two or more deoxyribonucleotides or ribonucleotides. The primer may be RNA or DNA, and may contain modified nitrogenous bases which are analogs of the normally incorporated bases, or which have been modified by attaching labels or linker arms suitable for attaching labels.

It will be apparent to those skilled in the art that primers and probes of the present invention in many cases are structurally similar or identical. The terms primer and probe refer to the function of the oligonucleotide. An oligonucleotide may function as a probe if it is hybridized to a target sequence to detect the target sequences. Alternatively, the same oligonucleotide may function as a primer if it is used to amplify the target.

As nucleic acids do not require complete homology to hybridize, it will be apparent to those skilled in the art that the primer sequences specifically disclosed herein may be modified so as to be substantially homologous to the primer sequences disclosed herein without loss of utility as specific primers for amplifying MOTT or MTB or *M. chelonae*. It is well-known in the art that hybridization of homologous and partially homologous nucleic acid sequences may be accomplished by appropriate manipulation of hybridization conditions to increase or decrease the stringency.

The oligonucleotides of the present invention are used to detect MOTT, MTB or *M. chelonae* nucleic acid sequences. However, the portion of the primer that hybridizes to the template may also be used as hybridization probe for direct detection of MOTT in various nucleic acid hybridization methods.

Alignment of the 16S-23S rDNA internal transcribed spacer sequences (ITSS) of MOTT species revealed considerably homology. Therefore, the present inventors designed several degenerate synthetic oligonucleotide primer pairs capable of amplifying selected regions of the ITSS of MOTT species.

The present invention provides a method for detecting 11 different MOTT by using primers capable of amplifying 11 different MOTT species in a single test and do not amplify *M. tuberculosis* DNA. In a preferred embodiment of the present invention, the MOTT primer pair consists of primers having nucleic acid sequences of SEQ. ID. NO.:3 and SEQ. ID. NO.:4. In another preferred embodiment of the present invention, the MOTT species detected by the primers having the nucleic acid sequence of SEQ. ID. No.:3 and SEQ. ID. NO.:4 are selected from the group consisting of *M avium, M. intracellularre, M. gordonae, M. simiae, M. kansaii, M. malmiennse, M. gastri, M. marimum, M. scrofulaceum, M. asiaticum,* and *M. szulgai*.

As used herein, the "template DNA" or "target sequences" refers to a nucleic acid sequence to which the amplification primer specifically binds and amplifies. These include the original nucleic acid sequence to be amplified and its complementary second strand as well as either strand of a copy of the original target sequence generated during the amplification reaction.

Copies of the target sequence which are generated during the amplification reaction are referred to as "amplified nucleic acid products" or "amplicons". An extension product refers to the copy of a target sequence produced by hybridization of a primer and extension of the primer by polymerase using the target sequence as a template.

In a preferred embodiment of this invention, amplification is by means of polymerase chain reaction using primer. The method of polymerase chain reaction is well known to those of skill in the art.

Alignment of the ITSS of MOTT species with *M. chelonae* revealed poor identity. However, alignment of the ITSS among *M. chelonae* isolates revealed 93% identity. Therefore, *M. chelonae* oligonucleotide primers (SEQ. ID. NO.:5 and SEQ. ID. NO.:6) were designed to amplify selected regions of the ITSS of *M. chelonae* and yield approximately a 192 bp product.

Another embodiment of the present invention provides a method for detecting *M. chelonae* comprising obtaining a sample that contains nucleic acid; amplifying the nucleic acid in the sample with primers having the nucleic acid sequence SEQ. ID. NO.: 5 and SEQ. ID. NO.: 6; and detecting amplified nucleic acid products produced in the amplification step, thereby detecting *M. chelonae* in the sample.

Preferably, the inventive methods disclosed herein employ a set of two amplification primers termed "primer sets" to amplify the mycobacterial nucleic acid sequences. Alternately, amplification using one primer or a set of three or more amplification primers can be used to carry out the present invention.

The present inventors designed the MOTT primers based on whether the primer: (i) selectively amplified MOTT DNA; (ii) did not amplify MTB; (iii) possessed the ability to amplify DNA of several MOTT species; (iv) produced a 120 to 200 bp product; and (v) produced minimal nonspecific amplification products. The primers designed to amplify MTB yielded approximately 180 bp fragment and specifically amplified MTB.

Therefore, the present invention further provides a method for detecting and differentiating the presence of MTB and MOTT comprising obtaining a sample containing nucleic acids; amplifying nucleic acid present in the sample by using two primer sets comprising a first primer set and a second primer set wherein the first primer set comprises primers having the nucleic acid sequence of SEQ. ID. NO.:1 and SEQ. ID. NO.:2; and the second primer set comprises primers having the nucleic acid sequence of SEQ. ID. NO.:3 and SEQ. ID. NO.:4; separating the amplified nucleic acid products; detecting amplified nucleic acid products having approximately 180 bp thereby indicating the presence of MTB in the sample; and detecting amplified nucleic acid products produced having approximately 130 bp thereby indicating the presence of MOTT in the sample.

The amplified nucleic acid products may be separated by any separation method known in the art including but not limited to electrophoresis and chromatography.

The present invention further provides a method for distinguishing the presence of MOTT species comprising obtaining a sample containing nucleic acids; amplifying nucleic acid present in the sample by using two primer sets comprising a first primer set and a second primer set wherein the first primer set comprises primers having the nucleic acid sequence of SEQ. ID. NO.:3 and SEQ. ID. NO.:4; and the second primer set comprises primers having the nucleic acid sequence of SEQ. ID. NO.:5 and SEQ. ID. NO.:6; separating the amplified nucleic acid products; detecting amplified nucleic acid products having approximately 130 bp thereby indicating the presence of MOTT in the sample; and detecting amplified nucleic acid products produced having approximately 190 bp thereby indicating the presence of *M. chelonae* in the sample.

Alternatively, the primers may be labeled with any detectable marker known in the art, including other radioactive nuclides such as $^{35}S$ or $^{32}P$ and the like, fluorescent markers such as fluorescein or rhodamine, and the like, or with enzymatic markers which may produce detectable signals when a particular chemical reaction is conducted, such as alkaline phosphatase or horseradish peroxidase. Such enzymatic markers are preferably heat stable, so as to survive the denaturation steps of the amplification process. Primers may be indirectly labeled by incorporating a nucleotide covalently linked to a hapten or other molecule such as biotin to which a labeled avidin molecule may be bound, or digoxygenin, to which a labeled anti-digoxygenin antibody may be bound. Primers may be labeled during chemical synthesis or the label may be attached after synthesis by methods known in the art. The method of labeling and the type of label is not critical to this invention.

In yet another embodiment, the present invention provides a method for distinguishing the presence of MOTT species comprising; (a) obtaining a sample containing nucleic acids; (b) amplifying nucleic acid present in the sample by using two primer sets comprising a first primer set and a second primer set wherein (i) the first primer set comprises primers having the nucleic acid sequence of SEQ. ID. NO.:3 and SEQ. ID. NO.:4; and (ii) the second primer set comprises primers having the nucleic acid sequence of SEQ. ID. NO.:5 and SEQ. ID. NO.:6; wherein each primer set is labeled with different labels; (c) separating the amplified nucleic acid products; (d) detecting incorporation of labeled primers from step (b)(i) thereby indicating the presence of MOTT in the sample; and (e) detecting incorporation of labeled primers from step (b)(ii) thereby indicating the presence of *M. chelonae* in the sample.

In still another embodiment, the present invention provides a method for detecting and differentiating the presence of MTB and *M. chelonae* comprising; (a) obtaining a sample containing nucleic acids; (b) amplifying nucleic acid present in the sample by using two primer sets comprising a first primer set and a second primer set wherein (i) the first primer set comprises primers having the nucleic acid sequence of SEQ. ID. NO.:1 and SEQ. ID. NO.:2; and (ii) the second primer set comprises primers having the nucleic acid sequence of SEQ. ID. NO.:5 and SEQ. ID. NO.:6; wherein each primer set is labeled with different labels; (c) separating the amplified nucleic acid products; (d) detecting incorporation of labeled primers from step (b)(i) thereby indicating the presence of MTB in the sample; and (e) detecting incorporation of labeled primers from step (b)(ii) thereby indicating the presence of *M. chelonae* in the sample.

In yet another embodiment, the present invention provides a method for detecting and differentiating the presence of MTB, MOTT and *M. chelonae* comprising; (a) obtaining a sample containing nucleic acids; (b) amplifying nucleic acid present in the sample by using three primer sets comprising: (i) the first primer set, a second primer set and a third primer set wherein (i) the first primer set comprises primers having the nucleic acid sequence of SEQ. ID. NO.:3 and SEQ. ID. NO.:4; (ii) the second primer set comprises primers having the nucleic acid sequence of SEQ. ID. NO.:3 and SEQ. ID. NO.:4; and (iii) the third primer set comprises primers having the nucleic acid sequence of SEQ. ID. NO.:5 and SEQ. ID. NO.:6; wherein each primer set is labeled with different labels; (c) separating the amplified nucleic acid products; (d) detecting incorporation of labeled primers from step (b)(ii) thereby indicating the presence of MTB in the sample; (e) detecting incorporation of labeled primers from step (b)(ii) thereby indicating the presence of MOTT in the sample; and (f) detecting incorporation of labeled primers from step (b)(iii) thereby indicating the presence of *M. chelonae* in the sample.

In one embodiment of the present invention, the label is selected from the group consisting of radioactive, enzymatic, fluorescent, biotinylated, and chemiluminescent labels.

The present invention further provides kits for detecting MOTT in a sample. In one embodiment, this invention provides a kit for detecting MOTT and MTB nucleic acid, wherein the kit comprises a container means comprising two primers sets wherein first primer set comprises primers having the nucleic acid sequence of SEQ. ID. NO.:1 and SEQ. ID. NO.:2; and second primer set comprises primers having the nucleic acid sequence of SEQ. ID. NO.:3 and SEQ. ID. NO.:4, wherein each primer set is labeled with different detectable labels; and a reagent for detecting said labels.

Another embodiment provides a kit for detecting MOTT and *M. chelonae* nucleic acid, wherein the kit comprises a container means comprising two primers sets wherein first primer set comprises primers having the nucleic acid sequence of SEQ. ID. NO.:3 and SEQ. ID. NO.:4; and second primer set comprises primers having the nucleic acid sequence of SEQ. ID. NO.:5 and SEQ. ID. NO.:6, wherein each primer set is labeled with different detectable labels; and a reagent for detecting said labels.

In yet another embodiment, the present invention provides a kit for detecting MTB and *M. chelonae* nucleic acid, wherein the kit comprises a container means comprising two primers sets wherein first primer set comprises primers having the nucleic acid sequence of SEQ. ID. NO.:1 and SEQ. ID. NO.:2; and second primer set comprises primers having the nucleic acid sequence of SEQ. ID. NO.:5 and SEQ. ID. NO.:6, wherein each primer set is labeled with different detectable labels; and a reagent for detecting said labels.

In still another embodiment, the present invention provides a kit for detecting MTB, MOTT and *M. chelonae* nucleic acid, wherein the kit comprises a container means comprising three primers sets wherein first primer set comprises primers having the nucleic acid sequence of SEQ. ID. NO.:1 and SEQ. ID. NO.:2; second primer set comprises primers having the nucleic acid sequence of SEQ. ID. NO.:3 and SEQ. ID. NO.:4; and third primer set comprises primers having the nucleic acid sequence of SEQ. ID. NO.:5 and SEQ. ID. NO.:6, wherein each primer set is labeled with different detectable labels; and a reagent for detecting said labels.

The following examples are given for the purpose of illustrating various embodiments of the invention and are not meant to limit the present invention.

7. MATERIALS AND METHODS

7.1 Sample Preparation

7.1.1 Fresh Tissue

Fresh tissue samples were prepared by chopping the tissue into fine pieces with sterile scissors and passing it through a hand operated disposable tissue grinder in a 50 mM Tris-HCl buffer, pH 8.0 containing 1 mM EDTA and 0.1% Tween 20.

7.1.2 Plueral, Synovial, Peritoneal and Pericardium Fluids

Plueral, synovial, peritoneal and pericardium fluids (5 to 50 ml) were concentrated by centrifugation fluid at 3,000×g for 25 minutes to 1 ml. These fluids contain high concentrations of protein. Therefore, a denaturing solution containing sodium hydroxide and triton was added to the sample to prevent protein agglutination. After boiling the samples to lyse the cells, the pH of the solution was adjusted to 7.0 to 7.5 using hydrochloric acid and Tris buffer. DNA was isolated from the neutralized lysate and concentrated using commercially available DNA isolating kits.

7.1.3 Whole Blood

*M. tuberculosis* was detected using whole blood by isolating buffy coats and lysing the bacterial cells. Buffy coats were suspended in digestion buffer (50 mM Tris-HCL buffer, pH 7.5 containing EDTA, 0.1% Tween 20 and 0.2 mg/ml of proteinase K) and incubated overnight in a water bath at 55° C.

7.1.4 Bone Marrow

Isolation of mycobacteria DNA from bone marrow was treated like fresh tissue (see Section 7.1.1). Bone marrow aspirates contain mostly bone marrow spicules which are separated from the blood by fine aspiration and digested. The DNA was isolated as described for buffy coats in Section 7.1.3.

7.1.5 Sputum, Spinal Fluids and Paraffin Embedded Tissue Sections

Mycobacteria cells from sputum, spinal fluids and urine samples were lysed by placing the sample in boiling water for 10 minutes.

Detection of mycobacteria when using paraffin-embedded tissue is performed using 25 μm slices of tissue block. The paraffin is removed using octane extraction and the octane is removed by performing repeated ethanol extractions. The tissue is digested using proteinase K with Tween 20. The cells were lysed by boiling and the DNA is isolated.

7.2 Nucleic Acid Extraction

The same extraction method was employed to extract nucleic acid from MTB and MOTT and the same sample was used for detection of MOTT, MTB and *Mycobacteria chelonae*. Initial processing steps were different for different types of samples (see Sections 7.1.1–7.1.5). Sample volumes were between 400–500 μl. Pure cultures of either *M. avium* or *M. gordonae* and *M. chelonae* cell were grown to a McFarland standard of about 3 to 4 in Middlebrook 7H9 broth (Difco) containing Tween 80 at 35° C. Cells suspensions of mycobacteria were used to extract genomic DNA. Genomic DNA was extracted by suspending cells in a boiling water bath for 10 minutes followed by adsorption of released DNA to charged glass beads from a Gene Clean kit (Bio 101, La Jolla, Calif.).

7.3 Primer Synthesis

The oligonucleotides of the present invention were obtained from GIBCO/BRL. All synthesized oligonucleotides have hydroxyl groups at the 5' end using β-cyanoethanol phoshoramidite chemistry. The oligonucleotides were purified by standard method using commercially available silica based columns by the manufacturer.

Oligonucleotide primers or oligonucleotide probes suitable for use in the present invention may be derived by any method known in the art, including chemical synthesis or cleavage of a larger nucleic acid using non-specific nucleic acid-cleaving chemicals or enzymes, or by using site-specific restriction endonucleases. The oligonucleotide primer may be purified by any method known in the art, including extraction and gel purification. The concentration and purity of the oligonucleotide primer may be examined on an acrylamide gel, or by measuring the optical densities at 260 and 280 nm in a spectrophotometer.

7.4 Polymerase Chain Reaction Conditions

The polymerase chain reaction was performed at 50° C.×10 minutes for one cycle; 94° C.×5 minutes for one cycle; 94° C.×30 seconds, 65° C.×30 seconds, 72° C.×45 seconds for 34 cycles; 72° C.×20 minutes for one cycle; and 4° C., until the samples were removed from the thermal cycler.

7.5 Detection of Mycobacteria

DNA size separation was accomplished by applying aliquots of the amplicons onto 8% native polyacrylamide gels using 44.5 mM tris-borate buffer, 1 mM EDTA, pH 8.3. Gels were dried using a commercially available gel dryer at approximately 80° C. for 30 minutes under vacuum. Visualization of the gels was performed by autoradiography using Kodak BioMax MR film. Quick detection of amplicons was visualized using a PhosphorImager because X-ray films often required overnight exposure at room temperature while PhosphorImager required only 60 minutes of exposure to obtain the same results.

In embodiments of this invention where DNA fragments are separated by length, any length separation means known in the art can be used. One alternative separation means employs a sieving medium for separation by fragment length coupled with a force for propelling the DNA fragments though the sieving medium. The sieving medium can be a polymer or gel, such a polyacrylamide or agarose in suitable concentrations to separate 10–1000 bp DNA fragments. In this case the propelling force is a voltage applied across the medium. The gel can be disposed in electrophoretic configurations comprising thick or thin plates or capillaries. The gel can be non-denaturing or denaturing. Alternately, the sieving medium can be such as used for chromatographic separation, in which case a pressure is the propelling force. Standard or high performance liquid chromatographic ("HPLC") length separation means may be used. An alternative separation means employs molecular characteristics such as charge, mass, or charge to mass ratio. Mass spectrographic means capable of separating 10–1000 bp fragments may be used. The choice of appropriate matrices and buffer are well known in the art and so are not described in detailed herein.

Alternatively, DNA fragments may be detected using labeled primers. In embodiments of this invention where DNA fragments must be labeled and detected, any compatible labeling and detection means known in the art can be used. In embodiments of this invention where intercalating DNA dyes are utilized to detect DNA, any such dye known in the art is adaptable. In particular such dyes include but are not limited to ethidium bromide, propidium iodide, Hoechst 33258, Hoechst 33342, acridine orange, and ethidium bromide homodimers.

7.6 Amplification of ITSS of MOTT

Several degenerate synthetic oligonucleotide primers were designed for amplification of selected regions of the ITSS of MOTT species (MAC, *M. gordonae*, *M. simiae*, *M. kansasii*, *M. malmoense*, *M. gastrii*, *M. marimum*, *M. scrofulaceum*, *M. asiaticum* and *M. szulgai*) based on nucleic acid homology. Primers were generated based on whether the primer: (i) selectively amplified MOTT DNA; (ii) did not amplify MTB; (iii) possessed the ability to amplify DNA of several MOTT species; (iv) produced a 120 to 200 bp product; and (v) produced minimal nonspecific amplification products.

Primer specificity was tested by PCR amplification of 0.01 to 0.1 ng of purified genomic DNA of *M. avium*, *M. kansaii* and *M. scrofulaceum* (see FIG. 1). Primers were 5'-end labeled with [γ-$^{32}$P] ATP. Radioactive amplicons generated from PCR amplification were separated on 8% nondenaturing polyacrylamide gels followed by autoradiography. The same conditions for genomic DNA purification, isolation and PCR amplification of the MTB complex and MOTT DNA were adopted. Amplification of *M. avium*, *M. kansaii* and *M. scrofulaceum* DNA with degenerate MOTT primer pair (SEQ. ID. NO.:3 and SEQ. ID. NO.:4, see Table I) yielded approximately 130 bp amplicon. PCR amplification of 10 ng of genomic DNA extracted from cells of *M. tuberculosis*, *M. bovis*, rapid mycobacteria growers (*M. chelonae* and *M. fortuitum*) and other bacteria (*Escherichia coli*, *Pseudomonas aeruginosa*, *Staphylococcus auerus*, *Klebsiella oxytoca*, *Enterococcus fecalis* and *Proteus vulgaris*) yielded no products with MOTT primers (SEQ. ID. NO.:3 and SEQ. ID. NO.:4) (see FIG. 1). Autoradiograph patterns of purified genomic DNA (0.1 ng) isolated from *M gordonae* was similar to patterns of purified genomic DNA (0.1 ng) isolated from *M. avium* (data not shown).

The MOTT PCR amplification method was tested on fifty clinical samples from bronchial washes, sputum, archival tissues and blood that were acid-fast positive and grew *M. avium*, *M. kansaii* or *M. scrofulaceum* upon culturing MOTT. DNA was extracted from clinical specimens as described above, see Section 7.1. DNA was amplified using radiolabeled MOTT primers (SEQ. ID. NO.:3 and SEQ. ID. NO.:4) and separated on 8% polyacrylamide gels. Autoradiography revealed approximately a 130 bp fragment (see FIG. 2). Both patient samples were positive for *M. avium*. (see FIG. 2, lane 3 acid-fast positive pleural fluid). Culture results were available 30 days after PCR results were known.

7.7 Amplification of ITSS of *M. chelonae*

An alignment of nucleic acid sequences of the ITSS of *M. chelonae* and *M. fortuitum* revealed poor species identity. However, alignment of the ITSS among *M. chelonae* revealed 93% identity while the nucleic acid homology among *M. fortuitum* isolates was only 53%. Therefore, based on nucleic acid homology, a *M. chelonae* oligonucleotide primer pair (SEQ. ID. NO.:5 and SEQ. ID. NO.:6) was designed to amplify selected regions of ITSS of *M. chelonae* and yield approximately a 192 bp product. The amplification potential of the *M. chelonae* (MC) primers were challenged using purified genomic DNA of *M. chelonae*, *M. fortuitum*, *M. avium*, *M. kansaii*, *M. scrofulaceum*, *M. tuberculosis* and *M. bovis*. The same conditions were employed for PCR amplification and amplicon detection with MOTT primers (SEQ. ID. NO.:3 and SEQ. ID. NO.:4) and MC primers (SEQ. ID. NO.:5 and SEQ. ID. NO.:6). PCR amplification of 0.01 ng of *M. chelonae* DNA yielded a single band of approximately 192 bp (see FIG. 3, lane 7). PCR amplification of 10 ng of DNA isolated from *M. tuberculosis*, *M. bovis*, MAC, *M. kanassi* and *M. scrofulaceum* yielded no product with MC primers (SEQ. ID. NO.:5 and SEQ. ID. NO.:6) (see FIG. 3, lanes 2 to 6). PCR amplification of genomic DNA isolated from other mycobacteria revealed no amplification products.

The potential of MC primer pair was tested on two specimens obtained from patients harboring *M. chelonae* infection. Genomic DNA was extracted from patient samples. DNA extraction and amplification with [γ-$^{32}$P] ATP labeled MC primers (SEQ. ID. NO.:5 and SEQ. ID. NO.:6), yielded approximately a 192 bp product. (see FIG. 4). Both patient samples were positive for *M. chelonae*. (see FIG. 4; lane 2 acid-fast positive BacTec bottle fluid smear). Culture results were available 10 days after PCR results were known.

TABLE 1

Primer Sequences

| SEQ. ID. NO.: | Sequences | Source |
|---|---|---|
| 1 | 5'-GGCTGTGGGTAGCAGACC | Artificial Sequence |
| 2 | 5'-CGGGTCCAGATGGCTTGC | Artificial Sequence |
| 3 | 5'-AAGGAGCACCACGARAAR | Artificial Sequence |
| 4 | 5'GTGTTGYCTCAGGRCCCAAT | Artificial Sequence |
| 5 | 5'CCATTTCCCAGCCGAATGAG | Artificial Sequence |
| 6 | 5'ACCACCAAGCAGGGTGACAA | Artificial Sequence |

R denotes A or G
Y denotes C or T

7.8 Standardization of PCR Methods

Specificity of PCR amplification with MOTT or MC primers was confirmed by amplifying template DNA with nonradioactive primers and cloning the PCR product into a TA-vector (Invitrogen Corporation). A fluorogenic probe labeled with fluorescent dyes (5'-carboxyfluoroscein at the 5'-end and N,N,N,N-tetramethy-6-carboxyrhodamine at the 3'-end) were prepared. The purified recombinant plasmid DNA was sequenced by automatic sequencing techniques and experimental nucleotide sequences were compared to published sequences of ITSS.

Positive controls included *M. avium* or *M. gordonae* cells. Slowing growing mycobacterial genome has one copy of the ITSS. MOTT amplicon was sequenced in three independent patient samples.

7.9 Identification of MOTT DNA in Clinical Samples

PCR amplification of template DNA extracted from several clinical specimens gave either a 130 bp amplicon with the MOTT primer set (SEQ. ID. NO.:3 AND SEQ. ID. NO.:4) (see FIG. 2) or approximately 192 bp amplicon with the *Mycobacteria chelonae* primer set (SEQ. ID. NO.:5 AND SEQ. ID. NO.:6) (see FIG. 4).

8. EXAMPLES

The invention having been described, the following examples are offered by way of illustration and not limitation.

The examples herein describe the successful detection and differentiation of infections in patient samples caused by *M. tuberculosis*, *M. chelonae* or MOTT. The ability to quickly detect *Mycobacterium tuberculosis* or mycobacterial infections other than tuberculosis obviated the need for unnecessary drug treatments or prolonged waiting periods for results.

8.1 Example I

Patient Characteristics: A seventy-five year old male living with his young grandchildren was diagnosed with prolonged respiratory problems and weight loss. His liver function was marginal and a mass was found in the left lower lobe of his lung as evidenced from a chest X-ray and computed tomography (CT). Histological examination of a biopsy of the suspected tissue region revealed adenocarcinoma. The patient was purified protein derivative (PPD) positive for tuberculosis.

A lobectomy of the lung was performed and several acid fast bacilli were revealed from the acid-stain of the lung smear. A tissue sample was sent for culturing but the results would not be available until 2 to 12 weeks. At this point, the clinician must determine whether the patient has *M. tuberculosis* or any other atypical mycobacteria before administering treatment as the patient lived with an extended family including small grandchildren. If the patient has tuberculosis, he must be treated immediately. However, the patient's poor health conditions prevented empirical treatments because some of the drugs used in the treatment of tuberculosis have side effects and are not tolerated by patients that require special attention. For example, isoniazid, a drug used in combination with other antibiotics for tuberculosis treatment has potential for liver damage. Additionally, the length of time for treatment can vary from 6 to 12 months. It is very difficult to treat small children with a drug regiment that lasts as long as 9 months.

Results: Two to six paraffin embedded tissue sections of 25 micron thickness were obtained for diagnosis. Template DNA was prepared as detailed in Section 7.2 and amplified for MTB and MOTT. The patient was positive for MOTT and negative for MTB.

8.2 Example II

Patient Characteristics: A 63 year old male was recently PPD positive and possessed pulmonary problems including emphysema. Chest X-rays patterns were abnormal and he was immunosuppressed due to a previous liver transplant.

Results: Pleural fluid and paraffin embedded tissue obtained from the patient was tested for MTB and MOTT. Template DNA was prepared as detailed in Section 7.1.5. The template was amplified for MTB and MOTT as described earlier. The patient was MTB negative and MOTT positive.

8.3 Example III

Patient Characteristics: A 92 year old female went to a primary care physician complaining of severe back problems. She was treated with steroids related for local pain. Three months later, she went to the hospital complaining of additional pain. A CT scan showed diskitis suggesting microbial infection.

Results: Microscopy analysis suggested that the fluid was acid-fast positive. Drainage fluid from the infected area was analyzed for MTB and MOTT. Within 24 hours, the fluid sample was diagnosed as positive for MTB and negative for MOTT using the present method.

8.4 Example IV

Patient Characteristics: A 54 year old male taking multiple drugs for asthma, heart and pulmonary problems came to the clinic complaining of a little bump on his scalp. Careful examination of the scalp revealed localized infection which did not penetrate the brain area.

Results: The fluid from the bump was acid-fast positive but was negative for both MTB and MOTT. Culture results revealed that the fluid was positive for *Nocardia* which is also an acid-fast organism.

8.5 Example V

Patient Characteristics: A 55 year old male patient taking steroid drugs for systemic lupus erytematosus possessed patchy nodules on his right forearm. The clinician was posed with a challenge to determine whether the cause of the patchy nodules was due to lupus which would require a more aggressive immunotherapy.

Results: A biopsy of the infected area was sent for histology, culturing and detection by PCR. The specimen was processed as a fresh tissue as detailed in Section 7.1.1. The extracted DNA was amplified using MTB, MOTT and MC primers. The specimen was positive fro MC but negative for MTB and MOTT. Because of the quick diagnosis, the patient was treated with clarithromycin, a single antibiotic without the need for an extra round of immunosuppressive drugs. Eight days later, the culture results also revealed *M. chelonae*.

All references cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

REFERENCES

1. Avantis-Aghajani, E., Jones, K., Holtzman, A., et al. Molecular techniques for rapid identification of mycobacteria. 1996 J. Clin. Microbiol. 34:98–102.
2. Badak, F. Z., Goksel, S., Sertoz R., et al. Use of nucleic acid probes for identification of Mycobacterium tuberculosis directly from MB/BacT bottles. 1999 J. Clin. Microbiol. 37:1602–1605.
3. Bartralot, R., Pujol, R. M., Garcia-Patos, V., et al. Cutaneous infections due to nontuberculous mycobacteria: histopathological review of 28 cases. Comparative study between lesions observed in immunosuppressed patients and normal hosts. 2000 J. Cutan Pathol. 27:124–129.
4. Brunello, F., Ligozzi, M., Cristelli, E., Bonora, s., Tortoli, E., Fontana, R. Identification of 54 Mycobacteria species by PCR-Restriction Fragment Length Polymorphism Analysis of the hsp65 gene. 2001 J. Clin. Microbiol. 39:2799–2806.
5. Chang, W. J., Tse, D. T., Rosa, R. H., Jr., Miller, D. Periocular atypical mycobacteria infection. 1999 Ophthalmology 106:86–90.

6. Chen, Z-H, Butler, W. R., Baumstark, B. R., Ahearn, D. G. Identification and differentiation of *Mycobacterium avium* and *M. intracellulare* by PCR. 1996 J. Clin. Microbiol. 34:1267–1269.
7. Covert, T. C., Rodgers, M. R., Reyes, A. L., Stelm,a G. N., Jr. Occurrence of nontuberculous mycobacteria in environmental samples. 1999 Appl. Environ. Microbiol. 65:2492–2496.
8. Dalovisio, J. R., Montenegro-James, S, S, Kemmerly, S. A., et al. Comparison of the amplified *Mycobacterium tuberculosis* (MTB) direct test, Amplicor MTB PCR, and IS6110-PCR for detection of MTB in respiratory specimens. 1996 Clin. Infect. Dis. 23:1099–1106.
9. Delaunois, L and Garrino, M. G. Manifestations, diagnosis and treatment of non-tuberculous mycobacterial infections in non-immunodepressed patients. 1997 Rev. Mal. Respir. 14 Suppl. 5:S130–S141.
10. DesJardin, L. E., Chen, Y, Perkins, M. D., Teixiera, L., Perkins, M. D., Cave, M. D., Eisenach, K. D. Comparison of the ABI 7700 system (TaqMan) and competitive PCR for quantification of IS6110 DNA in sputum during treatment of tuberculosis. 1998 J. Clin. Microbiol. 36:1964–1968
11. Eisenach, K. D., Sifford M. D., Cave, M. D., Bates, J. H., Crawford, J. T. Detection of mycobacterium tuberculosis in sputum samples using a polymerase chain reaction. 1991 Am. Rev. Respir. Dis. 144:1160–1163.
12. Emler, S., Feldman, K., Giacuzzo, V., Hewitt, P. L., Klapper, P. E., Lagrange, P. H., Witkins, E. W., Young, K. K. Y. and Hermann J-L. Multicenter evaluation of a patholgenic *Mycobacterium* screening probe. 2001 J. Clin. Microbiol. 39[7, 2687–2689.
13. Hellyer, T. J., DesJardin, L. E., Assaf, M. K., Bates, J. H., Cave, M. D., Eisenbach, K. D. Specificity of IS6110 based amplification assays for *Mycobacterium tuberculosis* complex. 1996 J. Clin. Microbiol. 34:2843–2846.
14. Hellyer, T. J., DesJardin, L. E., Teixeira, L., Perkins, M. D., Cave, M. D., Eisenbach, K. D. Detection of viable *Mycobacterium tuberculosis* by reverse transcriptase strand displacement amplification of mRNA. 1999 J. Clin. Microbiol. 37:518–523.
15. Herold, C. D., Fitzgerald, R. L., Herold, D. A. Current techniques in myycobacterial detection and speciation. 1996 Crit. Rev. clin. Lab. Sci. 33:83–138.
16. Horsburgh, C. R., Jr. and Cohn, D. L. *Mycobacterium avium* complex and the acquired immunodeficiency syndrome. 1986 Ann. Intern. Med. 105:968–969.
17. Horsburgh, C. R., Jr., Cohn, D. L., Roberts, R. B., et al. *Mycobacterium avium* and *M. Intracellulare* isolates from patients with or without acquired immunodeficiency syndrome. 1986 Antimicrob. Agents Chemother. 30:955–957.
18. Horsburgh, C. R., Jr., Caldwell, M. B., Simonds, R. J. Epidemiology of disseminated nontuberculous mycobacterial disease in children with acquired immunodeficiency syndrome. 1993 Pediatr. Infect. Dis. J. 12:219–222.
19. Kasai, H., Ezaki, T., Harayama, S. Differentiation of phylogenetically related slowly growing mycobacteria by their gvrB sequences. 2000 J. Clin. Microbiol. 38:301–308.
20. Kasai, H., Watanabe, K., Gasteiger, E. et al. Construction of the gyrB Database fir the identification and classification of bacteria. 1998 Genome Inform Ser Workshop Genome Inform 9:13–21.
21. Khoor, A., Leslie, K. O., Tazelaar, H. d., Helmers, R. A., Colby, T. V. Diffuse pulmonary disease caused by nontuberculous mycobacteria in immunocompetent people (hot tub lung). 2001 Am. J. clin. Pathol. 115:755–762.
22. Kirschner, P., Springer, B., Vogel, U., et al. Genotypic identification of mycobacteria by nucleic acid sequence determination: report of a 2-year experience in a clinical laboratory. 1993 J. Clin. Microbiol. 31:2883–2889.
23. Kox, L. F. F., Jansen, H. M., Kuijper, S., Kolk, A. H. J. Multiplex PCR assay for immediate identification of the infecting species in patients with mycobacterial disease. 1997 J. clin. Microbiol. 35:1492–1498.
24. Kulski, J. K., Khinsoe, c., Pryce, T., Christiansen, K. Use of a multiplex PCR to detect and identify *Mycobacterium avium* and *M. intracellulare* in blood culture fluids of AIDS patients. 1995 J. Clin. Microbiol. 33:668–674.
25. Lamps, L. W., Madhusudhan, K. T., Greenson, J. K. et al. The role of *Yersinia enterocolitica* and *Yersinia pseudotuberculosis* in granulomatous appendicitis: a histologic and molecular study. 2001 Am. J. Surg. Patholo. 25:508–515.
26. Lebrun, L., Espinase, F., Poveda, J. D. Vincent, V. Evaluation of nonradioactive DNA probes for identification of mycobacteria. 1992 J. Clin. Microbiol. 20:2476–2478.
27. Lumb, R., Goodwin, A., Ratcliff, R., Stapledon, R., Holland, A., Bastian, I. Phenotypic and molecular characterization of three clinical isolates of *Mycobacterium intejectum*. 1997 J. Clin. Microbiol. 35:2782–2785.
28. McGreedy, B. J., Callaway, T. H. Laboratory design and work flow. In Diagnostic Molecular Microbiology: Princciples and applications. Edited by Persing, D. H., Smith, T. F., Tenover, F. C., White, T. J. Washington, D.C. 1993 Amerian Society for Microbiology pp. 149–159.
29. Murray, P. R., Baron, E. J., Pfaller, M. A., Renover, F. C., Yolken, R. H. Manual of clinical microbiology. Washingotn, C., Amereican society Microbiology. Press 1999.
30. Park, H., Jang, H., Kim, C., Chung, B., Chang, C. L., Park, S. K. and Song, S. Detection and identification of mycobacteria by amplification of the internal transcribed spacer regions with genus and species-specific PCR primers. 2000 J. Clin. Microbiol. 38(11):4080–4085.
31. Phillips, M. S., von Reyn, C. F. Nosocomial Infection Due to Nontuberculous Mycobacteria. 2001 Clin. Infect.Dis. 33.
32. Ramos, L. S. Characterization of mycobacteria species by HPLC and pattern recognition. 1994 Chromatogr. 32:219–227.
33. Ringuet, H., Akoua-Koffi, C. Holtzman, A. et al. Molecular technique for rapid identification of mycobacteria. 1996 J. Clin. Microbiol. 34:98–102.
34. Ringuet, H., Akoua-Koffi, C. Honore, S. et al. hsp65 sequencing for identification of rapidly growing mycobacteria. 1999 J. Clin. Microbiol. 37:852–857.
35. Rish, J. A., Eisenach, K. D., Cave, M. D., Reddy, M. V., Gangadharam, P. R., Bates, J. H. Polymerase chain reaction detection of *Mycobacterium tuberculosis* in formalin-fixed tissue. 1996 Am. J. Respir. Crit. Care Med. 153: 1419–1423.
36. Roth, A., Fischer, M., Hamid, M. E., Michalke, S., Ludwig, W. and Mauch, H. Differentiation of phylogenetically related slowly growing mycobacteria based on 16S-23S rRNA gene internal transcribed spacer sequences. 1998 J. Clin. Microbiol. 36(1):139–147.
37. Salian, N. V., Rish, J. A., Eisenbach, K. D., Cave, M. D., Bates, J. H. Polymerase chain reaction to detect *Mycobacterium tuberculosis* in histologic specimens. 1998 Am. J. Respir. Crit. Care Med. 158:1150–1155.

38. Sambrok, J. Fritsch, E. F., Maniatis, T. Molecular Cloning: A Laboratory Manual. Cold Spring Harbor Laboratory Press, New York. 1998,
39. Smid, I., Salfinger, M. Mycobacteria identification by computer-aided gas liquid chromatography. 1994 Diagn. Microbiol. Infect. Dis. 19:88.
40. Springer, B., Stockman, L., Teschner, K., Roberts, G. d., Bottger, E. C. Tow laboratory collaborative study on identification of mycobacteria: molecular versus phenotype methods. 1996 J. Clin. Microbiol. 34:296–303.
41. Squier, C., UYu, V. L., Stout, J. E. Waterborne Nosocomial Infections. 2000 Curr. Infect. Dis. Rep. 2:490–496.
42. Stauffer, F. Haber, H. Rieger, A. et al. Genus level identification of mycobacteria from clinical specimens by using an easy t-to-handle *Mycobacterium*-specific PCR assay. 1998 J. Clin. Microbiol. 36:614–617.
43. Suara, R., Whitlock, J., Spearman, P. *Mycobacteria fortuitium* central venous catheter-related bacteremia in an infant with renal sarcoma. 2001. Pediatr. Hematol. Oncol. 18:363–365.
44. Telenti, A., Marchesi, F., Balz, M., Bally, F., Bottger, E. C., Bodmer, T. Rapid identification of mycobacteria to the species level of polymerase chain reaction and restriction enzyme analysis. 1993 J. Clin. Microbiol. 31:175–178.
45. Tevere, V. J., Hewitt, P. L., Dare, A., et al. Detection of *Mycobacterium tuberculosis* by PCR amplification with pan-*Mycobacterium* primers and hybridization to an *M. tuberculosis*-specific probe. 1996 J. Clin. Microbiol. 24:918–923.
46. Troesch, A., NNguyen, H., Miyada, C. G., et al. *Mycobacterium* species identification and rifampin resistance testing with high-density DNA probe arrays. 1999 J. Clin. Microbiol. 37:49–55.
47. Vejlgaard, T. B., Haahr, V., Peterslund, N. A. Atypical mycobacteria. Disseminated infection in patients with hematologic diseases. 1997 Ugeskr Laeger 159:5362–5367.
48. Wayne, L. G., Good, R. C., Krichevshy, M. I., et al. Fourth report of the cooperative, open-ended study of slowly growing mycobacteria by the International Working Group on Mycobacterial Taxonomy. 1991 Int. J. Syst. Bacteriol. 41:463–472.
49. Wolinsky, E. Mycobacterial diseases other than tuberculosis. 1992 Clin. Infect. Dis. 15:1–12.
50. Yule, A. Amplification-based diagnostics target TB. 1994 Biotechnology 12:1335–1337.
51. Zenone, T., Boibieux, A., Tigaud, S., et al. Non-tuberculous mycobacterial tenosynovitis: a review. 1999 Scand. J. Infect. Dis. 31:221–228.
52. Zolg, J. W., Phillipi-Schulz, S. The superoxide dismutase gene, a target for detection and identification of mycobacteria by PCR. 1994 J. Clin. Microbiol. 32:2801–2812.

---

What is claimed is:

1. A method for detecting the presence of mycobacteria other than tuberculosis (MOTT) comprising:
   (a) obtaining a sample containing nucleic acids;
   (b) amplifying nucleic acid present in said sample using primers having the nucleic acid sequence of SEQ. ID. NO.:3 and SEQ. ID. NO.:4; and
   (c) detecting amplified nucleic acid products produced in step (b) thereby detecting MOTT in said sample.

2. The method of claim 1, wherein said sample is selected from the group consisting of archival tissues, bronchial washes, sputum and blood.

3. The method of claim 1, wherein said nucleic acid is selected from the group consisting of DNA, RNA and mRNA.

4. The method of claim 1, wherein said MOTT is selected from the group consisting of *M. avium, M. intracellularre, M. gordonae, M. simiae, M. kansaii, M. malmiennse, M. gastri, M. marimum, M. scrofulaceum, M. asiaticum,* and *M. szulgai.*

5. A method for detecting the presence of *Mycobacteria chelonae* comprising:
   (a) obtaining a sample containing nucleic acids;
   (b) amplifying nucleic acid present in said sample using primers having the nucleic acid sequence of SEQ. ID. NO.:5 and SEQ. ID. NO.:6; and
   (c) detecting amplified nucleic acid products produced in step (b) thereby detecting *Mycobacteria chelonae* in said sample.

6. The method of claim 5, wherein said sample is selected from the group consisting of archival tissues, bronchial washes, sputum and blood.

7. The method of claim 5, wherein said nucleic acid is selected from the group consisting of DNA, RNA and mRNA.

8. A method for detecting and differentiating the presence of *mycobacteria tuberculosis* (MTB) and MOTT comprising:
   (a) obtaining a sample containing nucleic acids;
   (b) amplifying nucleic acid present in said sample using two primer sets comprising a first primer set and a second primer set wherein
       (i) said first primer set comprises primers having the nucleic acid sequence of SEQ. ID. NO.:1 and SEQ. ID. NO.:2; and
       (ii) said second primer set comprises primers having the nucleic acid sequence of SEQ. ID. NO.:3 and SEQ. ID. NO.:4;
   (c) separating said nucleic acid amplified from step (b);
   (d) detecting amplified nucleic acid produced in step (b) having approximately 180 bp thereby indicating the presence of MTB in said sample; and
   (e) detecting amplified nucleic acid produced in step (b) having approximately 130 bp thereby indicating the presence of MOTT in said sample.

9. The method of claim 8, wherein said biological sample is selected from the group consisting of archival tissues, bronchial washes, sputum and blood.

10. The method of claim 8, wherein said nucleic acid is selected from the group consisting of DNA, RNA and mRNA.

11. The method of claim 8, wherein said MOTT is selected from the group consisting of *M. avium, M. intracellularre, M. gordonae, M. simiae, M. kansaii, M. malmiennse, M. gastri, M. marimum, M. scrofulaceum, M. asiaticum,* and *M. szulgai.*

12. The method of claim 8, wherein said separating step consists of electrophoresis and chromatography.

13. A method for detecting and differentiating the presence of *mycobacteria tuberculosis* (MTB) and MOTT comprising:
  (a) obtaining a sample containing nucleic acids;
  (b) amplifying nucleic acid present in said sample using two primer sets comprising a first primer set and a second primer set wherein
    (i) said first primer set comprises primers having the nucleic acid sequence of SEQ. ID. NO.:1 and SEQ. ID. NO.:2; and
    (ii) said second primer set comprises primers having the nucleic acid sequence of SEQ. ID. NO.:3 and SEQ. ID. NO.:4;
  wherein each primer set is labeled with a different label;
  (c) separating said nucleic acid amplified from step (b);
  (d) detecting incorporation of labeled primers from step (b)(i) thereby indicating the presence of MTB in said sample; and
  (e) detecting incorporation of labeled primers from step (b)(ii) thereby indicating the presence of MOTT in said sample.

14. The method of claim 13, wherein said biological sample is selected from the group consisting of archival tissues, bronchial washes, sputum and blood.

15. The method of claim 13, wherein said nucleic acid is selected from the group consisting of DNA, RNA and mRNA.

16. The method of claim 13, wherein said MOTT is selected from the group consisting of *M. avium, M. intracellularre, M. gordonae, M. simiae, M. kansaii, M. malmiennse, M. gastri, M. marimum, M. scrofulaceum, M. asiaticum,* and *M. szulgai.*

17. The method of claim 13, wherein said separating step consists of electrophoresis and chromatography.

18. The method of claim 13, wherein said label is selected from the group consisting of radioactive, enzymatic, fluorescent, biotinylated and chemiluminescent labels.

19. A method for distinguishing species of MOTT comprising:
  (a) obtaining a sample containing nucleic acids;
  (b) amplifying nucleic acid present in said sample using two primer sets comprising a first primer set and a second primer set wherein
    (i) said first primer set comprises primers having the nucleic acid sequence of SEQ. ID. NO.:3 and SEQ. ID. NO.:4; and
    (ii) said second primer set comprises primers having the nucleic acid sequence of SEQ. ID. NO.:5 and SEQ. ID. NO.:6;
  (c) separating said nucleic acid amplified from step (b);
  (d) detecting amplified nucleic acid produced in step (b) having approximately 130 bp thereby indicating the presence of MOTT in said sample; and
  (e) detecting amplified nucleic acid produced in step (b) having approximately 190 bp thereby indicating the presence of *Mycobacteria chelonae* in said sample.

20. The method of claim 19, wherein said sample is selected from the group consisting of archival tissues, bronchial washes, sputum and blood.

21. The method of claim 19, wherein said nucleic acid is selected from the group consisting of DNA, RNA and mRNA.

22. The method of claim 19, wherein said MOTT is selected from the group consisting of *M. avium, M. intracellularre, M. gordonae, M. simiae, M. kansaii, M. malmiennse, M. gastri, M. marimum, M. scrofulaceum, M. asiaticum,* and *M. szulgai.*

23. The method of claim 19, wherein said separating step consists of electrophoresis and chromatography.

24. A method for detecting and differentiating the presence of MOTT species comprising:
  (a) obtaining a sample containing nucleic acids;
  (b) amplifying nucleic acid present in said sample using two primer sets comprising a first primer set and a second primer set wherein
    (i) said first primer set comprises primers having the nucleic acid sequence of SEQ. ID. NO.:3 and SEQ. ID. NO.:4; and
    (ii) said second primer set comprises primers having the nucleic acid sequence of SEQ. ID. NO.:5 and SEQ. ID. NO.:6;
  wherein each primer set is labeled with a different label;
  (c) separating said nucleic acid amplified from step (b);
  (d) detecting incorporation of labeled primers from step (b)(i) thereby indicating the presence of MOTT in said sample; and
  (e) detecting incorporation of labeled primers from step (b)(ii) thereby indicating the presence of *Mycobacteria chelonae* in said sample.

25. The method of claim 24, wherein said sample is selected from the group consisting of archival tissues, bronchial washes, sputum and blood.

26. The method of claim 24, wherein said nucleic acid is selected from the group consisting of DNA, RNA and mRNA.

27. The method of claim 24, wherein said MOTT is selected from the group consisting of *M. avium, M. intracellularre, M. gordonae, M. simiae, M. kansaii, M. malmiennse, M. gastri, M. marimum, M. scrofulaceum, M. asiaticum,* and *M. szulgai.*

28. The method of claim 24, wherein said separating step consists of electrophoresis and chromatography.

29. The method of claim 24, wherein said label is selected from the group consisting of radioactive, enzymatic, fluorescent, biotinylated and chemiluminescent labels.

30. A method for detecting and differentiating the presence of MTB and *Mycobacteria chelonae* in a biological sample comprising:
  (a) obtaining a sample containing nucleic acids;
  (b) amplifying nucleic acid present in said sample using two primer sets comprising a first primer set and a second primer set wherein
    (i) said first primer set comprises primers having the nucleic acid sequence of SEQ. ID. NO.:1 and SEQ. ID. NO.:2; and
    (ii) said second primer set comprises primers having the nucleic acid sequence of SEQ. ID. NO.:5 and SEQ. ID. NO.:6;
  wherein each primer set is labeled with a different label;
  (c) separating said nucleic acid amplified from step (b);
  (d) detecting incorporation of labeled primers from step (b)(i) thereby indicating the presence of MTB in said sample; and (e) detecting incorporation of labeled primers from step (b)(ii) thereby indicating the presence of *Mycobacteria chelonae* in said sample.

31. The method of claim 30, wherein said sample is selected from the group consisting of archival tissues, bronchial washes, sputum and blood.

32. The method of claim 30, wherein said nucleic acid is selected from the group consisting of DNA, RNA and mRNA.

33. The method of claim 30, wherein said separating step consists of electrophoresis and chromatography.

34. The method of claim 30, wherein said label is selected from the group consisting of radioactive, enzymatic, fluorescent, biotinylated and chemiluminescent labels.

35. A method for detecting and differentiating the presence of MTB, MOTT and *Mycobacteria chelonae* comprising:
(a) obtaining a sample containing nucleic acids;
(b) amplifying nucleic acid present in said sample using three primer sets comprising a first primer set; a second primer set; and a third primer set wherein
(i) said first primer set comprises primers having the nucleic acid sequence of SEQ. ID. NO.:1 and SEQ. ID. NO.:2;
(ii) said second primer set comprises primers having the nucleic acid sequence of SEQ. ID. NO.:3 and SEQ. ID. NO.:4; and
(iii) said third primer set comprises primers having the nucleic acid sequence of SEQ. ID. NO.:5 and SEQ. ID. NO.:6
wherein each primer set is labeled with a different label;
(c) separating said nucleic acid amplified from step (b);
(d) detecting incorporation of labeled primers from step (b)(i) thereby indicating the presence of MTB in said sample;
(e) detecting incorporation of labeled primers from step (b)(ii) thereby indicating the presence of MOTT in said sample; and
(f) detecting incorporation of labeled primers from step (b)(iii) thereby indicating the presence of *Mycobacteria chelonae* in said sample.

36. The method of claim 35, wherein said sample is selected from the group consisting of archival tissues, bronchial washes, sputum and blood.

37. The method of claim 35, wherein said nucleic acid is selected from the group consisting of DNA, RNA and mRNA.

38. The method of claim 35, wherein said MOTT is selected from the group consisting of *M. avium, M. intracellularre, M. gordonae, M. simiae, M. kansaii, M. malmiennse, M. gastri, M. marimum, M. scrofulaceum, M. asiaticum,* and *M. szulgai.*

39. The method of claim 35, wherein said separating step consists of electrophoresis and chromatography.

40. The method of claim 35, wherein said label is selected from the group consisting of radioactive, enzymatic, fluorescent, biotinylated and chemiluminescent labels.

41. A kit for detecting MOTT and MTB nucleic acid, wherein said kit comprises:
(a) a container means comprising two primers sets wherein first primer set comprises primers having the nucleic acid sequence of SEQ. ID. NO.:1 and SEQ. ID. NO.:2; and second primer set comprises primers having the nucleic acid sequence of SEQ. ID. NO.:3 and SEQ. ID. NO.:4, wherein each primer set is labeled with different detectable labels; and
(b) a reagent for detecting said labels.

42. A kit for detecting MOTT and *Mycobacteria chelonae* nucleic acid, wherein said kit comprises:
(a) a container means comprising two primers sets wherein first primer set comprises primers having the nucleic acid sequence of SEQ. ID. NO.:3 and SEQ. ID. NO.:4; and second primer set comprises primers having the nucleic acid sequence of SEQ. ID. NO.:5 and SEQ. ID. NO.:6, wherein each primer set is labeled with different detectable labels; and
(b) a reagent for detecting said labels.

43. A kit for detecting MTB and *Mycobacteria chelonae* nucleic acid, wherein said kit comprises:
(a) a container means comprising two primers sets wherein first primer set comprises primers having the nucleic acid sequence of SEQ. ID. NO.:1 and SEQ. ID. NO.:2; and second primer set comprises primers having the nucleic acid sequence of SEQ. ID. NO.:5 and SEQ. ID. NO.:6, wherein each primer set is labeled with different detectable labels; and
(b) a reagent for detecting said labels.

44. A kit for detecting MTB, MOTT and *Mycobacteria chelonae,* wherein said kit comprises:
(a) a container means comprising three primers sets wherein first primer set comprises primers having the nucleic acid sequence of SEQ. ID. NO.:1 and SEQ. ID. NO.:2; second primer set comprises primers having the nucleic acid sequence of SEQ. ID. NO.:3 and SEQ. ID. NO.:4; and third primer set comprises primers having the nucleic acid sequence of SEQ. ID. NO.:5 and SEQ. ID. NO.:6, wherein each primer set is labeled with different detectable labels; and
(b) a reagent for detecting said labels.

45. The kit of claim 41, 42, 43 or 44, wherein said detectable label is selected from the group consisting of enzymatic, fluorescent, biotinylated and chemiluminescent labels.

* * * * *